(12) United States Patent
Wielinga et al.

(10) Patent No.: US 8,529,969 B2
(45) Date of Patent: *Sep. 10, 2013

(54) METHOD FOR MANUFACTURING PURE GUAR MEAL

(75) Inventors: Willem Cor Wielinga, Tagerwilen (CH); Jean-Marc Ricca, Paris (FR)

(73) Assignee: Meyhall AG, Kreuzlingen (CH)

( * ) Notice: Subject to any disclaimer, the term of this patent is extended or adjusted under 35 U.S.C. 154(b) by 1329 days.

This patent is subject to a terminal disclaimer.

(21) Appl. No.: 10/274,979

(22) Filed: Oct. 22, 2002

(65) Prior Publication Data

US 2003/0044479 A1 Mar. 6, 2003

Related U.S. Application Data

(63) Continuation of application No. 09/445,370, filed as application No. PCT/CH98/00256 on Jun. 11, 1998, now abandoned.

(30) Foreign Application Priority Data

Jun. 12, 1997 (EP) ..................................... 97810369

(51) Int. Cl.
*A61K 35/78* (2006.01)

(52) U.S. Cl.
USPC .......................................................... 424/776

(58) Field of Classification Search
USPC ................. 424/70.1, 70.11, 0.13, 70.13, 776; 514/77.2; 536/114
See application file for complete search history.

(56) References Cited

U.S. PATENT DOCUMENTS

| | | | | |
|---|---|---|---|---|
| 3,467,647 A | | 9/1969 | Benninga | |
| 3,912,713 A | * | 10/1975 | Boonstra et al. | 536/114 |
| 4,057,509 A | * | 11/1977 | Costanza et al. | 516/107 |
| 4,169,945 A | * | 10/1979 | DeGuia et al. | 536/114 |
| 4,320,226 A | * | 3/1982 | Tiefenthaler et al. | 536/114 |
| 4,645,833 A | | 2/1987 | Bayerlein et al. | |
| 4,874,854 A | * | 10/1989 | Colegrove et al. | 536/114 |
| 5,013,763 A | * | 5/1991 | Tubesing et al. | 514/772 |
| 5,489,674 A | * | 2/1996 | Yeh | 356/114 |
| 5,536,825 A | * | 7/1996 | Yeh et al. | 536/52 |
| 5,733,854 A | | 3/1998 | Chowdhary et al. | |
| 6,664,381 B1 | * | 12/2003 | Wielinga | 536/4.1 |

FOREIGN PATENT DOCUMENTS

| | | |
|---|---|---|
| DE | 19511568 A1 * | 10/1996 |
| DE | 19600225 A1 * | 7/1997 |
| EP | 0 130 946 | 1/1985 |
| EP | 0 246 854 | 11/1987 |
| EP | 0 432 951 | 6/1991 |
| EP | 0 465 992 | 1/1992 |
| EP | 0 686 643 | 12/1995 |
| EP | 0 686 643 A1 * | 12/1995 |
| WO | WO 9618376 A1 * | 6/1996 |
| WO | 97 11974 | 4/1997 |
| WO | WO 9723195 A1 * | 6/1997 |
| WO | WO 9739724 A1 * | 10/1997 |

OTHER PUBLICATIONS

CTFA Cosmetic Ingredient Dictionary, 3rd Edition, CTFA, 1982.
Typical Properties of Silicone Emulsions—Amine Functional from Dow Corning [online]. [retrieved on Apr. 6, 2001]. Retrieved from: http://www.dowcorning.com/page_generate.pl?id=7406.
Database WPI, XP002073157, abstracting JP 04 273 811 of Sep. 30, 1992, Section Ch,, Week 9246 Derwent Publications Ltd., London, GB.

* cited by examiner

*Primary Examiner* — Rei-tsang Shiao
(74) *Attorney, Agent, or Firm* — Sughrue Mion, PLLC

(57) ABSTRACT

A method for producing pure guar flour and the use of hydroxy propyl trimethyl ammonium chloride-guar flour obtained according to the method in clear aqueous cosmetic formulations which are intended to be applied on hair and/or skin and which can be washed out or rinsed off as conditioning agents or depositing agents to dilute cosmetic formulations.

18 Claims, 1 Drawing Sheet

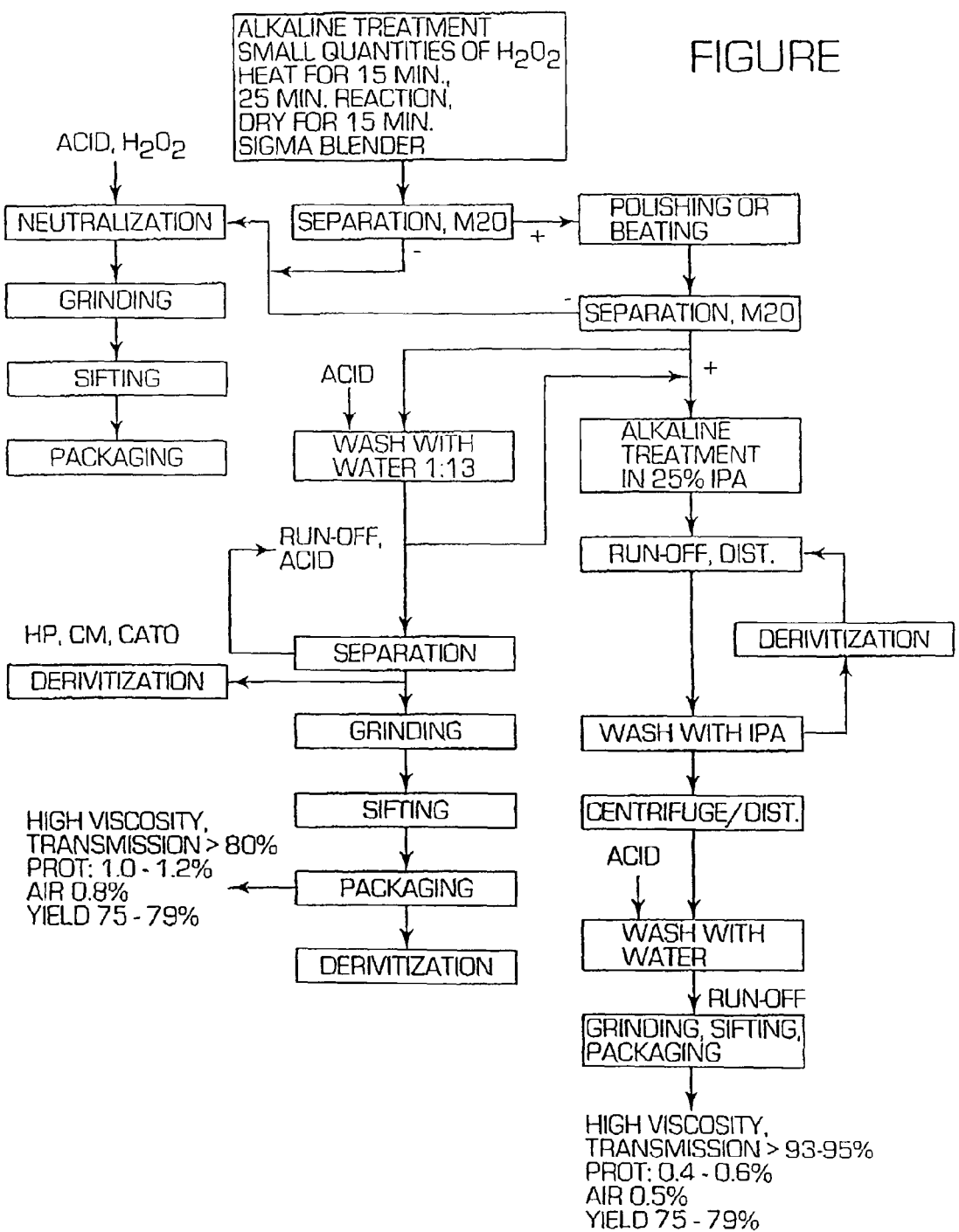
FIGURE

METHOD FOR MANUFACTURING PURE GUAR MEAL

CROSS REFERENCE TO RELATED APPLICATIONS

This is a continuation of application Ser. No. 09/445,370 filed Feb. 22, 2000 now abandoned, which is a National Stage Entry of PCT/CH98/00256 filed Jun. 11, 1998; the disclosure of which is incorporated herein by reference.

The invention relates to a process for the production of guar flour, which, if it is dissolved in water, yields a transparent solution of varying viscosity, i.e. low to very high, whereby the process supplies good yields of the pure flour in spite of extensive purification. Transparent, high-viscosity solutions of pure guar flour are primarily of great significance in the foodstuffs industry.

Guar flour is used as a thickening agent in the textile and explosives industries, as a binding agent in the paper industry, as a flocculent in ore production, as an aid in the extraction of natural gas and petroleum, in the pharmaceutical and cosmetic fields and as a thickening agent, emulsifier and co-stabilizer in foodstuffs.

In pharmaceuticals, low viscosity guar flour is used for spray-embedding vitamins, for example, in order to increase their storage stability. Beyond that, the use of guar flour in sprays guarantees a nearly monomolecular distribution of the substance and a resulting even re-absorption, which is desirable in the case of asthma medications and various anti-allergics. Due to the extraordinarily low protein content of the pure guar flour, there is no danger of developing an allergic reaction to a medication containing this substance. Additional applications in this field are the formulation of retard tablets and use as an agent for reducing cholesterol levels. In the field of medicines, very viscous guar flour is also used as a stabilizer in contrast media.

Guar flour has also proven itself as, among other things, an ideal dietetic agent, since its components, the so-called galactomannans, are not affected by enzymes of the human stomach and small intestines. This is to be expected, since in the re-absorbing part of the human digestion system neither β-mannanase nor β-mannosidase nor α-galactosidase is present, which would be necessary to break down these components. Since the components of the guar flour are not involved in the human metabolism, guar flour is in no way to be viewed as a carrier or supplier of calories. Since guar flour is composed of completely neutral polysaccharides, i.e. galactomannans, which have neither uronic acid nor other ionic groups, they represent completely harmless material from a physiological standpoint.

A further advantage with regard to its use as a food supplement is its complete taste neutrality. It is used in calorie-reducing or fat-reducing foods or drinks, which are frequently felt by the consumer to be "thin". The addition of pure guar flour to these products lends a "creamy" consistency to them. Guar flour is used in the production of fruit juices in order to re-suspend the fruit pulp evenly, in puddings and cremes it is used as a thickener, and in ice creams, milkshakes, mousse and similar products it is used as a stabilizer.

With standard guar flour preparations, only a slight molecular interaction was ever recorded with the biopolymer xanthane. Although in mixing these two colloids, a synergistic increase in viscosity indeed occurred, a specific gel formation as in the case of carubin, however, did not occur with carob flour and xanthane. If one heats up mixtures in a ratio of 1:1 of the guar flour obtained according to the invention and xanthane and lets them cool at 4° C. (refrigerator temperature), a soft gel forms. An advantage of this combination of guar flour and xanthane consists in that the gel from these two components melts at body temperature and is therefore exceptionally well-suited for the production of jelly-type foods, as a carrier substance in the administration of medications and the like. Guar flour and xanthane are also used together as co-stabilizers in the production of salad dressings, since this combination, in contrast to guar flour used by itself, is acid-resistant.

Guar flour is obtained from the endosperm of the guar seed (*cyamopsis tetragonobolus*). Guar flour consists primarily of galactomannans, i.e. polysaccharides the main chain of which is linked in the 1->4 direction by β-glycosidic bonds and is composed of mannose that is partially linked to galactose through primary OH groups. The ratio of non-substituted mannose to mannose substituted with galactose is approximately 2:1, wherein the substituted units are not strictly alternating, but instead are arranged in groups of two or three in the polygalactomannan molecules. The guar-galactomannans form highly viscous solutions even in low concentrations with water. 1 percent-by-weight solutions of commercially standard guar flour in water yield viscosities of approximately 3,000 to 6,000 mPa·s.

Guar-galactomannans, because of chemical and physical-chemical differences, have been subdivided into galactomannans soluble in cold water, galactomannans soluble in hot water and insoluble galactomannans.

To obtain and purify the guar flour, the guar-seed is mechanically treated, whereby about 35 parts of unpurified guar endosperm halves and about 60 parts of guar flour are obtained. The guar flour consists essentially of the germ of the seed, the scraped-off seed hulls and small endosperm parts. The endosperm completely envelops the germ and in turn is surrounded by the seed hull. At the point of contact between the endosperm and seed hull, there is a protein rich, aleuron-like cell layer, the cells of which are tightly interlocked with the endosperm.

The unpurified endosperm halves can be further purified mechanically and supply splits of varying quality with regard to their protein content, their components that cannot be hydrolyzed by acid (A.I.R.) and the husk content. The characterization "split" typical in professional circles is interchangeable with the term "endosperm halves".

Although guar flour already has broad application, it is desirable to improve its degree of purity and along with this its physical and physiological characteristics. The purity of the guar flour is of great importance, in particular for its application in the foodstuffs field. Likewise desirable is a better utilization of the neutral, non-ionic main components of the endosperm, so that these can increasingly be used in the corresponding industrial sectors instead of cellulose derivatives that dissolve clear in water, other polysaccharides or synthetic polymers that dissolve clear in water.

If the products currently available on the market, consisting of pure guar flour processed into flour, are dissolved in water for 10 minutes at 25° C. or 86 to 89° C., turbid solutions are obtained. If the insoluble material of these solutions is centrifuged with high force (>35,000×g), it turns out that 23-35% of the guar flour consists of insoluble material.

Microscopic studies have shown that the spun out material is primarily composed of hull fragments, protein bodies, insoluble peripheral cells, intact, non-enclosed cells of the inner-endosperm and other seed or split impurities. A known chemical derivation of guar flour by etherization, carboxymethylization, hydroxypropylation, a combination of these and cationization makes it possible to produce products with significantly improved solubility in water and with it accordingly higher transparency of the solutions.

One of the processes previously used to obtain pure guar flour uses chlorinated solvents, such as trichloroethylenes (see EP 0 130 946, Meyhall Chemical AG). The suspension was fractionated by simply letting it stand or by centrifuging, wherein a protein-rich fraction (floating fraction) developed and a protein-poor fraction (settling fraction) precipitated.

It was shown that the floating fraction of ground endosperm, such as guar CSA 200/50 can contain up to 25% proteins and the settling fraction, which makes up 75% of the pure flour, contains about 1.5 to 1.6% protein. The settling fraction is, for example, suitable for the production of cationic derivatives, which, after being dissolved, yield clear aqueous solutions. A disadvantage of this process is that finely milled hull fragments are likewise found in the settling fraction.

A further disadvantage is the use of halogenated solvents, since a specific weight of 1.47 to 1.48 kg/l is required. Proteins possess a density of 1.3 kg/l and the galactomannans a density of 1.5 to 1.55 kg/l, depending upon the particular moisture content. The guar flour produced with the described process is only appropriate for technical applications; this guar flour cannot be used in the foodstuffs field since residues of the halogenated solvent used (10 ppb were detected in fractions extracted with ethanol) remain in the end product. Halogenated solvents are toxic and caustic to various degrees and frequently contain allergenic characteristics. Also for environmental reasons, one should refrain from this process.

A further process for the production of pure guar flour was proposed as early as 1969. It consisted of an alkali treatment of pre-soaked splits at increased temperatures, wherein 100 parts of alkali were absorbed by 100 parts of SPS. The large quantity of alkali, i.e. NaOH, had to be washed out. This was done with cold water in a ratio of one part SPS (single purified splits) to 80 parts $H_2O$ and in a dehydration step with isopropanol (IPA) in which the residual NaOH of the purified splits was neutralized by acetic acid.

After the milling a pure guar flour of high quality was obtained in a yield of 60-70%, based on the raw material SPS (single purified splits). In 1969, this process was further developed by Stein, Hall & Co., Long Island City, N.Y., until it was ready for industrial use. The washing process at that time of the carboxymethylated, hydroxypropylated or cationized guar flour (guar ether) or combinations thereof with water were based on this process. The purpose of this process of purifying guar derivatives is to remove hull fragments and peripheral cell layers, as well as to remove by-products of the various etherization reactions (hydropropylation, carboxymethylation, cationization and/or combinations thereof).

Another known process for the production of pure guar flour is the treatment of guar splits with acid. This process supplies a product of outstanding quality; i.e. the resulting material supplies yields, when dissolved in water, solutions of great clarity with simultaneously greater viscosity. However, a disadvantage of this process consists in the relatively expensive procedure with multiple washing and neutralization steps. Moreover, special apparatuses that make the process very costly are needed for an acid treatment.

In spite of the extensive purification process described above, there has been no success thus far in obtaining a non-derivative guar flour in an economical and environmentally friendly manner that yields a clear, aqueous solution with high viscosity with simultaneously good yields.

The disadvantages of the previous procedure for purifying and obtaining pure guar flour are:

1. Large losses of valuable endosperm parts in the mechanical purification and, as a result, lower yields of pure guar flour in relation to the original material;
2. Hull fragments, which are still found at the various split qualities and to a large extent disturb the functionality of the modified end products;
3. Peripheral, protein-rich cells of the aleuron layer that barely swell in water and likewise negatively influence the functionality of the end products;
4. Presence of other impurities of the guar seeds such as wood particles, which must not be present;
5. High environmental impact It was therefore urgently desired to develop a process for the production of pure guar flour that remedies the above-mentioned disadvantages and supplies a pure guar flour in good yields that, after its dispersion in water, results in a highly viscous solution that is primarily used in the foodstuffs industry, pharmaceutical, dyes and paints industries and oil extraction, to name a few examples.

It is the purpose of this invention to fulfill the above-cited requirements, i.e. to obtain good yields of pure guar flour that is pure and particularly well-suited to the foodstuffs industry by a new production process that yields low to highly viscous clear aqueous solutions.

The process according to the invention for the production of pure guar flour includes the following stages:
(a) Treatment of guar-splits with a base in the presence of small quantities of hydrogen peroxide
(b) Partial neutralization of the alkali splits with an acid
(c) Mechanical removal of the peripheral cells
(d) If necessary, double washing with water
(e) Treatment of the splits with an aqueous alcohol solution An initial precondition for obtaining pure guar flour is the improvement of the starting material, the so-called splits. The splits covered with a hull constitute up to 42.5 percent by weight of the seed. The hull-endosperm overlapping parts, which amount to 13.5% by weight of the seed, are essentially insoluble in water. The germ of the seed encompasses the remaining 44%. These quantity specifications show that the theoretical yields of splits that can be used for the invention without hull and without overlapping parts amounts to 32%.

The pure guar flour obtained according to the invention is most advantageously produced from splits that have a protein content of 4.2% and an A.I.R. portion of 1.8%.

Such splits can be produced after an alkaline treatment using 10 to 40% caustic soda, preferably 33%, at room temperatures, but preferably at increased temperatures.

The difference of this process, novel in relation to the previously known ones, which likewise include an alkaline treatment of the starting material, consists in the addition of low concentrations of hydrogen peroxide during the alkaline treatment. This chemical "peeling" supplies splits from which the hull cells can be removed very easily and nearly completely with mechanical means. By treating the splits with, for example, 8-10 parts of 33% caustic soda and 1.1 parts 35% hydrogen peroxide, the peripheral cells of the splits are attacked and can be removed by mechanical abrasion. The polysaccharides of the cell layers found under the peripheral cells are not oxidized since the amount of the hydrogen peroxide used is too low.

The splits purified in this way, which can optionally be washed with water or processed further unwashed, can still be significantly improved for the purposes of the invention, in that phospholipids and other "non-polar" substances are washed out. This results in a greater clarity of the product dissolved in water and is achieved by treatment of the purified product with an aqueous alcohol solution, preferably aqueous isopropanol (IPA), at increased temperatures. With products not washed with water, an addition of more caustic soda before the treatment with isopropanol is not necessary since the product still contains about 4-7% NaOH. If the product was washed, the addition of an alkaline solution is necessary. After the isopropanol treatment, the alkaline splits are washed with water and milled at a desired moisture content.

The degree of hydration during the milling significantly influences the characteristics of the milled end product. The higher the moisture content during grinding in a technically workable mass, the greater the quantity of polysaccharides to become dissolved, i.e. the yield of active galactomannans is that much higher. This can be explained by the expansion of the cell volume due to the high amount of moisture. During the milling, the swollen cells are forced through a defined opening or crack, whereby the cell membrane can tear, assuming that the swollen particles are significantly larger than the openings (the elasticity of the cells likewise plays an important role). In the production of solutions in water, the galactomannans are released from the cells destroyed in this way, which is not the case with cells that are not destroyed. In these cases, the galactomannans remain inside the intact cells and do not contribute effectively to the viscosity of the solution.

A moisture content of about 82%, preferably 72 to 75%, is acceptable in milling for practical and technical reasons. Moisture contents lower than 72% in milling affect the quality of the guar flour. A content higher than 82% causes technical problems.

A great advantage of this invention lies in the 25% recovery of the abraded peripheral cell layers, i.e. in an extreme reduction of the environmental impact.

An additional advantage of the present invention lies in the simplification of the process. Only a few less steps are necessary to obtain a pure product with higher solubility and viscosity.

Another advantage of this invention consists in the possibility of producing products for solutions with viscosities, for example, as low as 35 mPa·s and such as are measured up to 6000 to 9,000 mPa·s with a 1% concentration in water at 25° C.

Another advantage of the invention consists in producing pure guar products, the protein content of which is as low as 0.2 to 0.5%.

The greatest advantage of this invention, however, consists in that the previous standard purification processes are essentially simplified and shortened, whereby the production of pure guar flour becomes substantially more cost-effective.

Moreover, the new process is exceptionally environmentally friendly, since about 25% of the sifted peripheral cell layers can be recovered. The abrasion that results in the process described here can furthermore be used in textile printing as a thickening agent. This means an optimal utilization of the starting material.

A derivation of the galactomannans of the guar flour is of significance for its cold water solubility. Through the derivation (e.g. carboxylmethylation, hydropropylation, cationization, etc.) one or more non-ionic, anionic or cationic groups are added, whereby the etherized hard-to-access galactomannans can be dissolved even at 25° C. The derivation typically occurs in succession to the purification. The use of the derived guar flour, however, is not allowed in food application. However, derived guar flour, in particular cation-active guar flour, is used in cosmetic products such as hair conditioner, body lotions and in similar use.

Especially included in particular in the cationic guar flour derivatives, which can be produced from a pure guar flour obtained by the process according to the invention, are the hydroxypropyltrimethyl ammonium chloride guar flours.

These can be obtained by etherization of a pure guar flour under basic conditions and under an inert gas atmosphere with 2,3-epoxypropyl-trimethyl-ammonium chloride as a cationic etherization agent and by subsequent purification and separation.

The etherization can preferably be performed in two main steps:

an initial step, in which the cationic etherization agent is diffused in the guar flour under alkaline conditions and under an inert gas atmosphere at a temperature from around 20 to 55° C., preferably around 30 to 50° C., and then suspended in an aqueous alcohol solution, in particular a water-isopropanol-solution that contains 25 to 70% by weight of isopropanol, and a second, actual etherization step under an inert gas atmosphere at a temperature of about 50 to 70° C., especially preferred at a temperature of about 60 to 65° C.

The first step (the diffusion) can in particular be conducted in the presence of sodium hydroxide, whereby of 100 parts of guar flour, approximately 1 to 4 parts by weight are accounted for by sodium hydroxide; this step can last 15 to 60 minutes.

The second step (the actual etherization) can last approximately 45 to 120 minutes.

The resulting cationic product is next brought into contact with air again at the same temperature conditions in order to slightly depolymerize the product to the desired end viscosity. The product is then purified one or more times by washing with an aqueous alcoholic solution, in particular water/isopropanol. After the pH has been adjusted with an acid, e.g. acetic acid, the cationic guar flour is separated, for example by filtration or centrifuging, and then dried.

The quantity of etherization agent that can be used is selected so that one obtains a cationic guar flour with a degree of substitution (SG) within the range of 0.01 to 0.4. The degree of substitution (SG) can be defined as the number of substituents of 2,3-epoxypropyl-trimethyl ammonium chloride that is added per hexose unit of guar flour.

The hydroxypropyl-trimethyl ammonium chloride guar flours can have an average molecular weight of about 50,000 to 8,000,000.

The cationic guar flour obtained by the process according to the invention, in particular the hydroxypropyl-trimethyl ammonium chloride guar flours, can be used in particular for the production of cosmetic formulations.

The invention thus also relates to the use of a hydroxypropyl-trimethyl ammonium chloride guar flour produced by etherization of a guar flour obtained by the process according to the invention in clear aqueous cosmetic formulations that are specified for use on hair and/or skin and are to be washed out or rinsed off as a conditioning agent and/or as a deposition aid for additional conditioning agents in the dilution of these cosmetic formulations.

One understands "clear aqueous cosmetic formulations" to be any cosmetic formulation that contains at least 60% by weight of water and has a transparency of at least 92% at 600 nanometers.

These clear cosmetic formulations can in particular be present in the form of a conditioning shampoo, a shower gel or a liquid soap.

For an advantageous embodiment of the invention, this hydroxypropyl-trimethyl ammonium chloride guar flour has a degree of substitution of about 0.01 to 0.4, preferably from about 0.05 to 0.25 and an average molecular weight of about 50,000 to $3 \times 10^6$.

It can be used in a quantity that corresponds to 0.05 to 0.5%, preferably 0.1 to 0.3% of the weight of these cosmetic formulations.

Along with the hydroxypropyl-trimethyl ammonium chloride guar flour, there can be still other conditioning agents. These can in particular be non-volatile silicons (polyorganic siloxanes) with a viscosity from 10,000 to $10^6$ mPa·s in the form of particles with a diameter of under 35 nanometers, preferably from about 20 to 25 nanometers.

These silicons are preferably used in the form of a pre-formed aqueous dispersion, which can have a concentration from about 20 to 60% by weight, preferably from about 30 to 50% by weight. They can also be used in the cosmetic formulations in a quantity of about 0.1 to 1% by weight, preferably from about 0.5 to 1% by weight of ingredient in relation to the weight of the cosmetic formulation.

As silicones, polydimethyl-siloxane oils, phenylated silicon oils (diphenyl-dimeticones) and animated silicon oils (amodimeticones) can be named.

Finally, the invention relates to clear aqueous cosmetic formulations that are specified for use on hair and/or skin and are to be washed out or rinsed off, whereby these formulations contain (in terms of weight) the following:

about 8 to 30% by weight, preferably 10 to 20% by weight, at least of a non-ionic, anionic, amphoteric or zwitterionic tenside, expressed as active substance;

about 0.05 to 0.5% by weight, preferably about 0.1 to 0.3% by weight, of hydroxypropyl-trimethyl ammonium chloride guar flour derivative of a guar flour produced by the process according to the invention, in some cases about 0.1 to 1% by weight, preferably about 0.5 to 1% by weight, at least of a non-volatile silicon in an aqueous emulsion, the particle size of which is less than 35 nanometers, preferably about 20 to 25 nanometers, expressed as ingredient, and at least 60% by weight of water, preferably at least 75% by weight of water.

The clear aqueous cosmetic formulations according to the invention have a transparency of at least 92% at 600 nanometers.

Falling under the non-ionic, anionic, amphoteric or zwitterionic tensides that can be present, are the following:

anionic tensides such as:

Alkyl sulfates of the formula $ROSO_3M$, in which R represents a $C_{10}$-$C_{24}$ alkyl or hydroxy alkyl radical, preferably a $C_{12}$-$C_{20}$ alkyl or hydroxy alkyl radical, and especially preferred a $C_{12}$-$C_{18}$ alkyl or hydroxy alkyl radical, M represents a hydrogen atom or a cation as described above and its ethylene oxide (EO) derivative and/or propylene oxide (PO) derivative with an average of 0.5 to 6, preferably 0.5 to 3 EO units and/or PO units;

Salts of saturated or unsaturated $C_8$-$C_{24}$ fatty acids, preferably $C_{14}$-$C_{20}$ fatty acids, $C_9$-$C_{20}$ alkyl-benzene sulfonate, primary or secondary $C_8$-$C_{22}$ alkyl sulfonates, alkyl glycerine sulfonates, sulfonated polycarboxylic acids as described in GB-A-1 082 179, paraffin sulfonates, N-acyl-N-alkyl taurates, alkyl phosphate esters and/or alkylether phosphate esters and/or alkylarylether phosphate esters, isethionates, alkyl succinamates, alkyl sulfo succinates, alkyl glycoside sulfates, alkyl polyethoxy carboxylates; whereby the cation is an alkali metal or alkaline earth metal (sodium, potassium, lithium, magnesium), a possibly substituted ammonium radical (methyl-, dimethyl-, trimethyl-, tetramethylammonium, dimethyl-piperidinium, etc.) or an alkanoloamine derivative (monoethanolamine, diethanolamine, triethanolamine, etc.);

Alkyl sulfonic acid esters of the formula R—CH($SO_3M$)-COOR', whereby R signifies a $C_8$-$C_{20}$ alkyl radical, preferably a $C_{10}$-$C_{16}$ alkyl radical, R' signifies a $C_1$-$C_6$ alkyl radical, preferably a $C_1$-$C_3$ alkyl radical and M represents an alkali metal cation (sodium, potassium, lithium), in some cases substituted ammonium (methyl-, dimethyl-, trimethyl-, tetramethyl-ammonium, dimethyl-piperidinium, etc.) or an alkanolamine derivative (monoethanolamine, diethanolamine, triethanolamine, etc.). Especially preferred are the sulfonic acid methylesters with a radical R of $C_{14}$ through $C_{16}$;

Alkyl amide sulfates of the formula $RCONHR'OSO_3M$, in which the R represents a $C_2$-$C_{22}$ alkyl radical, preferably a $C_6$-$C_{20}$ alkyl radical, R' represents a $C_2$-$C_3$ alkyl radical, M represents a hydrogen atom or a cation as defined above and its ethylene oxide (EO) derivatives and/or propylene oxide (PO) derivatives with an average of 0.5 to 60 EO and/or PO units;

Alkyl and dialkyl phosphates and phosphate ethers;

non-ionic tensides such as polyalkoxylated aliphatic $qC_8$-$C_{22}$ alcohols with 1 to 25 alkylene oxide units (ethylene oxide, propylene oxide);

for example TERGITOL 15-S-9, TERGITOL 24-L-6 NMW, sold by: Union Carbide Corp., NEODOL 45-9, NEODOL 23-65, NEODOL 45-7, NEODOL 45-4, sold by: SHELL CHEMICAL CO., KYRO EOB, sold by: THE PROCTER & GAMBLE CO. are cited;

glucosamide, glucamide;

the alkyl polyglycosides and their polyalkylene oxide derivatives described in U.S. Pat. No. 4,565,647;

polyalkoxylated (polyethoxylated, polypropyloxylated, polybutoxylated) alkyl phenols, the alkyl substitute of which is $C_6$-$C_{12}$ alkyl and which contain 5 to 25 alkylene oxide units; for example, TRITON X-45, X-114, X-100 or X-102, sold by: ROHM & HAAS CO. are named;

glycerine amide derivatives of N-alkylamines (U.S. Pat. No. 5,223,179 and FR-A-1 585 966);

condensation products from ethylene oxide or propylene oxide with propylene glycol, ethylene glycol and/or glycerine, like the PLURONIC series, sold by BASF;

condensation products from ethylene oxide or propylene oxide with ethylene diamin, like the TETRONIC series, sold by BASF;

Aminoxides such as $C_{10}$-$C_{18}$ alkyl dimethylamine oxides, $C_8$-$C_{22}$ alkoxyethyl-dihydroxy-ethylamine oxides;

$C_8$-$C_{20}$ fatty acid amides;

ethoxylated fatty acids;

ethoxylated fatty acid amides;

ethoxylated amines;

ethoxylated amidoamines, especially those that are derived from the N-hydroxyethyl-N'-alkylamide-ethylene diamins;

amphoteric and zwitterionic tensides such as

Alkylbetaine, alkyl dimethyl-betaines, alkyl-amidopropyl-betaines, alkyl-amidopropyl-dimethyl-betaines, alkyl-trimethyl-sulfo-betaines, imidazoline derivatives such as alkyl-amphoacetates, alkyl-amphodiacetates, alkyl-amphodiproprionates, alkyl sultains or alkyl-amidopropyl-hydroxysultains, condensation products from fatty acids and protein hydrolysates, amphoteric alkyl-polyamine derivatives such as AMPHOLIC XL, sold by: RHONE-POULENC, AMPHOLAC 7T/X and AMPHOLAC 7C/X, sold by: BEROL NOBEL.

These tensides are selected from a series of anionic tensides such as alkylsulfates and/or alkylsulfate ethers, preferably in combination with at least one amphoteric tenside such as alkylamidopropylbetains and/or alkylamphoacetates or -diacetates and, if applicable, in combination with at least one non-ionic tenside such as the polyalkoxylated aliphatic alcohols and/or glucamides and/or alkylglucosides.

A tenside mixture consisting of the following is particularly preferred for these cosmetic formulations:

approximately 5% to approximately 20%, preferably between approximately 10% to approximately 15% of at least one anionic tenside, especially an alkylsulfate and/or an alkylsulfate ether;

approximately 0.1% to 15%, preferably between approximately 1% to approximately 5% of at least one amphoteric tenside, especially alkylamidopropylbetain and/or alkylamphoacetate or -diacetate and approximately 0% to 5%, preferably between approximately 1% to approximately 3% of at least one non-ionic tenside, especially a polyalkoxylated aliphatic alcohol and/or a glucamide and/or an alkylglucoside;

whereby the percentages mean percent in weight of the active tenside in the cosmetic formulations.

These clear aqueous cosmetic formulations may also contain other additional ingredients that are selected in such a way as not to decrease the clarity of these formulations.

These invented cosmetic formulations may also contain the following:

- up to 10%, preferably up to 5% polymer derivatives that have a protective or moisturizing action on the skin or a conditioning action, such as modified celluloses (e.g., hydroxymethylcellulose, carboxymethylcellulose) or non-ionic derivatives (e.g., hydroxypropyl guar flour), non-ionic derivatives (e.g., carboxymethyl guar flour) or non-ionic/anionic derivative mixtures such as carboxyhydroxypropyl guar flour; however, substitute or additional synthetic polymers such as polyacrylate or synthetic cationic polymers that are known by the general CTFA designation "polyquaternium," such as the polymer MIRAPOL A15 or MIRAPOL 550 from Rhone-Poulenc or polymers that bestow dressing properties such as vinyl pyrrolidon copolymers may be added;
- up to 5% moisture retaining agents or moisturizers, especially like glycerine;
- up to 5% calcium complexing agents like citrate ions;
- up to 1% sunscreen filters such as octylmethoxycinnamate (PARSOL LCX from GIVAUDAN);
- up to 0.3% bactericides such as triclosan or chlorphenesine;
- up to 1% preservatives such as p-hydroxybenzoic acid methyl ester, -ethyl ester, and -butyl ester; sodium benzoate; or GERMABEN (trade name);
- up to 0.5% thickening agents, gelling agents, or stabilizers like the linked polyacrylates CARBOPOL sold by GOODRICH, xanthan gum, succinoglycan derivatives;
- —perfumes, pigments.

The material that results from the present invention is particularly advantageous; because it can be dissolved in water, it yields solutions of greater clarity. A 1% solution (0.9% solid matter) of this pure guar flour manufactured using this new process has a viscosity of 6000 to 9000 mPa·s at 25° C. An aqueous solution transparency of up to 95% can be achieved.

The viscosity was determined using a Brookfield RTV viscosity meter; the transparency of the solution by means of a photospectrometer.

The invention will be explained by means of several examples below. Splits of the highest quality were used as the source material for the examples described.

From these examples it may be seen that treatment of the periphery of the guar splits with a sodium hydroxide solution of optimized concentration in the presence of small amounts of hydrogen peroxide already leads to the elaboration of pure guar products.

These pure products demonstrate a viscosity of 5000 to 9000 mPa·s at a 1% concentration as well as clarity greater than 80% at a 0.5% concentration and a 1 cm light path at 500 nm, whereas conventional guar products in aqueous solution demonstrate light transmission of between 45% to 48%.

This transparency to light can be achieved even without treatment with isopropanol. With isopropanol, light transparency of up to 98% is achieved because isopropanol removes phospholipids that cannot be removed by washing with water.

After this first cleansing, the alkaline splits demonstrate a water content of 12% to 15%.

The splits are washed twice with water in a ratio of 1:7 and 1:6 over a period of 6 and 8 minutes respectively.

In the process, the splits absorb water up to 70% and can then either be ground or further modified after additional water has been added so that a moisture content of 76% to 78% is reached.

However, it is possible to treat the splits without the washing step.

The ground products possess a protein content of 1.0% to 1.2% and an AIR percentage of approximately 0.8. Depending on the quality of the source material, the yield from these products is 75% to 79%.

EXAMPLE I 370 guar splits with a galactomannane content of at least 84% are treated for example in a preheated sigma mixer with 10% NaOH (84 ml of a 33% NaOH solution) and then after one minute, additionally with 4 ml of a 35% $H_2O_2$ solution that was diluted with 20 ml isopropanol. The reaction temperature is indirectly increased by means of 90° C. hot water to 70° C. and then kept constant for 30 minutes.

Then a portion of the caustic solution present is neutralized by 21 g of 96% $H_2SO_4$, diluted with 8 g of water. The mixing process is continued another 16 minutes at 70° C. Then, 70 g of water are quickly added in order to more easily remove the treated, disruptive peripheral cell layers during the mixing process. The mixing process is carried out for 30 minutes at 70° C.

The reaction mixture is sifted through a M20 sieve, and in so doing, 95 g −M20 ($H_2O$: 16.2%) and
360 g +M20 ($H_2O$: 12.9%)
are obtained.

The +M20 fraction displays a NaOH content 5-6% and is washed twice with cold water, in each case using 6 parts tap water to 1 part of the unwashed +M20 fraction.

The washing process was carried out 5 or, respectively, 6 minutes while intensively stirring.

The washed, swelled splits are recovered by simple sifting.

(The alkali treatments mentioned in literature and patent literature using 20-32% NaOH require a washing water quantity of more than 40 parts tap water per 1 part unwashed splits.)

916 g of swollen splits with a water content of 73.3% were recovered after cleaning with water.

A viscosity of 7,000 mPa·s was measured at 20 rpm and 25° C., after the homogenous solution, obtained by impact, of the swollen splits had cooled overnight.

The 1% aqueous solution was produced in a household mixer at the highest speed at roughly 90° C. The quantity of swelled splits to be dissolved was calculated at a water content of 10%.

A 1:1 dilution of this 1% solution yields a light transmission of 81.3% up to 500 nm in a 1-cm cuvette.

N.B.

If 40% less NaOH and 40% less $H_2SO_4$ are used (under otherwise identical conditions), less abrasion (roughly 12%) and a significantly lower light transmission of roughly 75% are obtained.

EXAMPLE II

These products obtained according to Example I can be significantly improved in their quality (viscosity, transparency) by further decreasing their protein and A.I.R. content. Products that are not washed with water may be treated for 30-60 minutes with 25 percent by weight isopropanol at 65 to 70° C. without adding additional caustic solution, because the splits still contain approx. 5-6% NaOH. If washed splits are used, the adding of 2-5% caustic solution, preferably caustic soda, is required.

Following the aqueous isopropanol treatment, the alkaline splits are washed, brought to the necessary moisture level by adding more water, and ground.

The transparency of the aqueous solution of such products is 93 to 95%. The viscosity of a 1% aqueous solution can be set at 6,000 to 7,000 mPa·s depending on reaction conditions.

The product designated as −M20 and cleaned in the above-described manner is a guar gum with a viscosity of 1,000 to 1,500 mPa·s at 1% concentration, which can serve as the basis for significantly improved guar products or derivatives.

The −M20 fraction as well can also be processed for applications that use alkaline oxidized guar products or derivatives. A field of application would be polyester printing, for example. By using the −M20 fraction, the material to be printed obtains a soft hand after the dispersion dyes used have been fixed at extremely high temperatures.

EXAMPLE III 8,522 g of guar splits with a galactomannane content of at least 84% are brought into contact, for example in an indirectly heatable Drais mixer, with 2,580 g of a 33% NaOH solution that was preheated to 74° C.

After 3 minutes, 230 g of a 14% $H_2O_2$ solution are slowly added.

The temperature of the heterogenous reaction mixture is increased to and maintained at 70° C. for 30 minutes.

To better control the partial neutralization with 668 g of a 69.5% sulfuric acid, the reaction mixture is then cooled down to 55° C.

The reaction is continued 30 minutes at 70° C. The treated guar splits are then washed with cold tap water for 5 minutes, using 12 parts tap water for 1 part unwashed splits. In the reaction in the aforementioned mixer, practically no abrasion is produced, in such a way that a sifting process before the washing can be dispensed with.

The washed splits have a water content of 72% and are ground finer than M150 in the usual manner in a hot air current in a swing-hammer crusher.

The ground product still contains roughly 2% NaOH and shows a viscosity of 4,200 mPa·s at a concentration of 1%, based on 10% water with a 6.8 pH.

The clarity of a 0.5% solution which, was measured as described, is 82.4%.

EXAMPLE IV 25 kg of guar splits of the same quality as used in Examples I and II are treated for a half hour at 70° C. in a sigma mixer with 9% NaOH in the presence of 0.67 kg of a 14.1% $H_2O_2$ solution. A 33% solution was used.

The peripheral cell layers were then abraded for 15 minutes at 70° C. in an open reactor 6.5 percent of weight −M20 can be removed.

The −M20 fraction was washed with tap water as described, yielding a product with a viscosity of 5,700 mPa·s (1% concentration) and a clarity (0.5%) of 81.3%.

The still adhering, treated peripheral cell layers can be abraded mechanically by an intensive rubbing of the +M20 fraction, e.g., in a household coffee grinder at the lowest grinding speed.

By repeated "grinding", roughly 12% of the peripheral cell layers could be additionally removed, in such a way that a total of roughly 18-19% of the −M20 fraction was recovered.

These peripheral cell layers can also be abraded in aqueous alcohols with intensive stirring.

If, for example, 1 part of the +M20 fraction is intensively stirred for 5 minutes in 1.2 parts 35 percent by weight of methyl alcohol and this process is repeated 3 times, 13.5% of the −M20 fraction can be recovered, in such a way that a total of 20% of this fraction is preserved.

EXAMPLE V

Cationic Derivatization

The product from Example III was ground and 400 g of this ground product was re-suspended in 1600 g of a 25 percent by weight of aqueous isopropanol solution. One hundred ml of a 30 percent by weight of NaOH solution was added. The suspension was heated to 70° C. in a nitrogenous atmosphere for 30 minutes while constantly stirring. This reaction temperature was maintained for 1 hour, then the suspension was cooled down to 55° C. The stirring was interrupted and after the reaction product was precipitated, the excess was poured off.

The reaction product was washed with 1,000 ml of a 50 percent by weight isopropanol solution and then treated with 10 ml of glacial acetic acid in order to neutralize a stoichiometric quantity of NaOH.

The excess was poured off after the reaction product was precipitated. 7.8 g NaOH was removed in this way.

225 g of a 40 percent by weight 2,3-epoxypropyl trimethyl ammonium chloride solution was added and left to penetrate into the alkaline-treated product for 1 hour at 30° C. Afterward, 1,100 ml of an 85 percent by weight isopropanol solution was used as suspension medium. The nitrogen atmosphere was reestablished and the suspension was heated to 65° C. This temperature was kept constant for 40 minutes.

The reaction product thus comes into contact with atmospheric oxygen so that the final viscosity of the cationic guar product could be controlled.

The reaction was carried out 45 minutes at 65° C. The product was then washed with 800 ml of a 85 percent by weight of isopropanol solution and then with 1,000 ml of the same solution. During the washing process, 25 ml of 99 percent by weight glacial acetic acid was added, whereby the caustic solution was neutralized.

The product was recovered by filtration and dried with hot air at 70° C.

This cationic guar displayed a 880 mPa·s viscosity (based on 10% moisture) at 1% concentration in water and a light transmission (clarity) of 94.2%.

EXAMPLE VI

Carboxymethylation 350 g of a +M20 fraction with a moisture level of 7.5% was moistened with 100 ml of cold water. After 15 minutes, the majority of the monochloroacetate-Na solution consisting of 79 g of monochloroacetate-Na and 184 g water was slowly added while stirring for 24 minutes. The remaining 100 ml of this solution was quickly added for 5 minutes. The adding of the reagents took place at room temperature.

After 16 more minutes of incubation while stirring, the temperature was increased to 50° C. Then, 27 g of NaOH pellets was added. Due to the exothermic reaction of the NaOH pellets used, the temperature quickly increased to 65-66° C. and was maintained there for 36 minutes.

The reaction product was removed from the reactor and washed twice with water in a ratio of 1:6. Due to the very rapid water absorption of the cleaned carboxymethyl splits not treated with borax, their dwell time in water was limited to 2 minutes in each case. The weight of the highly swelled splits was 2,640 g. A dehydration step with isopropanol (1,500 g was used) was therefore necessary.

3,261 g of the filtrate was recovered. The weight of the alcohol-moistened, carboxymethylated splits was 879 g with a volatility 66.8%.

Since no precautions were taken by means of an inert nitrogen dome during the reaction, the splits were in contact with air throughout the reaction, which caused a considerable depolymerization.

The viscosity of a 1% solution of the carboxylated splits was 1,720 mPa·s with a clarity of 92.7%. These values were obtained at a temperature 25° C.

EXAMPLE VII

Four hundred grams of the preferred guar split quality with a galactomannane content of at least 84% was first diluted in a preheated sigma mixer with 4 ml of 35% $H_2O_2$, treated for 9 minutes with 21 ml of demineralized water, after which 40 g of NaOH dissolved in 61 ml of demineralized water was added hot.

Within 3 minutes, the reaction mixture attained the desired temperature of 68° C. The reaction temperature of 68°-72° C. was maintained for 20 minutes. Most of the water was then drawn off from the reaction mixture by ventilation and indirect heating for 23 minutes.

The reaction mixture was sifted through M20, thus obtaining 30 g of −M20 and 437 g of +M20 (10.1% $H_2O$ content). The +M20 fraction was washed twice with water, in each case using 6 parts tap water to 1 part of the unwashed +M20 fraction. The respective washing times were 4 and 5 minutes.

The washed, swollen splits were recovered by simple sifting; 892 g of swollen splits were obtained that had a water content of 67.8%. These splits were placed in solution in typical manner and this solution produced a viscosity of 2,300 mPa·s and a light transmission of 86.4% (measured according to the description in Example I).

FIG. 1: The flow chart shows the treatment, according to the invention, of the splits with caustic solution and hydrogen peroxide and the further processing possibilities following the alkaline treatment.

EXAMPLE VIII

Clear Conditioning Shampoo

A clear conditioning shampoo with the following composition is produced according to the method known by the experts:

| Components | g (of active ingredient)/100 g |
|---|---|
| Sodium laurethyl-2-sulfate (aqueous solution of sulfatized ethoxylated lauryl alcohol with 28% active ingredient) | 7.5 |
| Cocoamidopropyl betaine (aqueous solution with 25% active ingredient) | 2.5 |
| Hydroxypropyl trimethyl ammonium chloride guar gum from Example 5 (100% active ingredient) | 0.3 |
| Water ad 100 | |

This formulation is set at a viscosity of 3,000 mPa·s by adding sodium chloride.

The transparency measured for 600 nm is 97%.

EXAMPLE IX

Clear Shower Gel

A clear shower gel with the following composition is produced according to the method known by the experts (adding of the micro-emulsion of amino-modified silicon to the rest of the mixture):

| Components | g (of active ingredient)/100 g |
|---|---|
| Sodium laurethyl-2-sulfate (aqueous solution of sulfatized ethoxylated lauryl alcohol with 28% active ingredient) | 8 |
| Cocoamidopropyl betaine (aqueous solution with 25% active ingredient) | 4 |
| Hydroxypropyl trimethyl ammonium chloride guar gum from Example 5 (100% active ingredient) | 0.2 |
| MIRASIL ADME (RHODIA CHEMICALS) (aqueous amodimeticone micro-emulsion with 30% active ingredient and a particle size of 25 nm) | 0.3 |
| Water ad 100 | |

This formulation is set at a viscosity of 2,500 mPa·s by adding sodium chloride.

The transparency measured for 600 nm is 96%.

The invention claimed is:

1. A process for making derivatized guar gum comprising the following steps:
   preparing non derivatized pure guar flour by the following steps (a) to (e)
   (a) chemically peeling peripheral cells layers of guar splits by treating guar splits with an alkaline solution in the presence of hydrogen peroxide at 65 to 70° C. to obtain alkaline splits;
   (b) optionally partially neutralizing the alkaline splits with an organic or inorganic acid;
   (c) mechanically removing peripheral cells layers of the guar splits;
   (d) optionally treating the splits with an aqueous alcohol solution; and
   (e) grinding the splits into flour,
   subjecting the non derivatized pure guar flour to a derivatization by means of carboxy methylation, hydroxy propylation, or cationization, or combinations thereof.

2. A process according to claim 1 wherein said guar flour is etherized with 2,3 epoxypropyltrimethyl ammonium chloride as a cationic etherizing agent, under basic conditions and in an inert gas atmosphere, followed by purification and separation to obtain a hydroxypropyltrimethyl ammonium guar gum.

3. A process according to claim 2, wherein the etherization comprises:
an initial step, in which the cationic etherizing agent is diffused in the guar flour, under alkaline conditions and in an inert gas atmosphere at a temperature from 20 to 55° C., and is then suspended in an aqueous alcohol solution, and a second step, in which the actual etherization is performed in an inert gas atmosphere at a temperature of 50 to 70° C.

4. A process according to claim 3, wherein the initial step is conducted at a temperature of 30 to 50° C., the aqueous alcohol solution employed in the initial step is a water-isopropanol solution containing 25 to 70% by weight isopropanol, and the second step is conducted at a temperature of 60 to 65° C.

5. A process for making derivatized guar gum comprising the following steps:
preparing non derivatized pure guar flour by the following steps (a) to (e)
(a) chemically peeling peripheral cells layers of guar splits by treating guar splits with an alkaline solution in the presence of hydrogen peroxide at 65 to 70° C. to obtain alkaline splits;
(b) optionally partially neutralizing the alkaline splits with an organic or inorganic acid;
(c) mechanically removing peripheral cells layers of the guar splits;
(d) optionally treating the splits with an aqueous alcohol solution; and
(e) grinding the splits into flour,
to obtain a product that demonstrates a viscosity of 5000 to 9000 mPa at a 1% concentration
subjecting the non derivatized pure guar flour to a derivatization by means of carboxy methylation, hydroxy propylation, or cationization, or combinations thereof.

6. A process according to claim 1, wherein the alkaline solution employed in step (a) is caustic soda, in a quantity of 6-10%, as based on the guar splits.

7. A process according to claim 1, wherein the quantity of hydrogen peroxide used in step (a) is 0.175 to 0.35% by weight and a hydrogen peroxide solution of 35% by weight is employed.

8. A process according to claim 1, comprising step (b) and wherein the acid in step (b) is an inorganic acid.

9. A process according to claim 8, wherein the acid used in step (b) is sulfuric acid employed in a concentration of 60 to 80% by weight.

10. A process according to claim 9, wherein the sulfuric acid is employed in a concentration of 70% by weight.

11. A process according to claim 8, wherein the acid used in step (b) is phosphoric acid employed in a concentration of 60 to 85% by weight.

12. A process according to claim 11, wherein the phosphoric acid is employed in a concentration of 75% by weight.

13. A process according to claim 1, comprising step (b) and wherein the acid in step in (b) is sulfuric acid, phosphoric acid or acetic acid.

14. A process according to claim 13, wherein the acid in step in (b) is acetic acid.

15. A process according to claim 1, comprising step (d) and wherein the alcohol solution employed in step (d) is an aqueous solution of ethanol, methanol, or isopropanol.

16. A process according to claim 15, wherein the alcohol solution employed in step (d) is an aqueous solution of isopropanol.

17. A process according to claim 16, wherein the aqueous alcohol solution employed in step (d) is a 20 to 40% by weight isopropanol solution.

18. A process according to claim 17, wherein the aqueous alcohol solution employed in step (d) is a 25% by weight isopropanol solution.

* * * * *